(12) United States Patent
Cordier et al.

(10) Patent No.: US 6,509,495 B1
(45) Date of Patent: Jan. 21, 2003

(54) SELECTIVE HYDRODEHALOGENATION METHOD

(75) Inventors: Georges Cordier, Francheville (FR); Roland Jacquot, Francheville (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/857,678

(22) PCT Filed: Dec. 7, 1999

(86) PCT No.: PCT/FR99/03031

§ 371 (c)(1), (2), (4) Date: Jul. 19, 2001

(87) PCT Pub. No.: WO00/35834

PCT Pub. Date: Jun. 22, 2000

(30) Foreign Application Priority Data

Dec. 11, 1998 (FR) .............................................. 98 15684

(51) Int. Cl.[7] ........................ C07C 305/00; C07C 51/00; C07C 17/10; C07C 22/00
(52) U.S. Cl. ........................ 562/113; 562/125; 562/604; 562/605; 500/144; 500/176
(58) Field of Search ................................ 570/176, 144; 562/113, 125, 604, 605

(56) References Cited

U.S. PATENT DOCUMENTS 4,873,381 A    10/1989   Kellner

FOREIGN PATENT DOCUMENTS

| EP | 0657 413 | 6/1995 |
| EP | 0 726244 | 8/1996 |
| GB | 1 364 495 | 8/1974 |

OTHER PUBLICATIONS

Miyashita 0 et al; studies on Fluorinated Pyrimidines, IV Stereochemistry of 6–alkoxy–5–fluoro–5,6–dihydrouracils and 5–a alkoxycarbonyl–5–fluoro–6–substitued–5, 6–dihydrouracils Chemical and Pharmaceutical Bulletin, vol. 30, No. 7, Jul. 1982, pp. 2333–41 XP–002112749.

Primary Examiner—Alan Siegel

(57) ABSTRACT

The invention concerns a selective hydrodehalogenation method characterised in that it comprises a step which consists in contacting a substrate including a sp 3 hybridisation carbon atom bearing an electro-attracting group and at least a fluorine atom, and a halogen atom heavier than fluorine, with a reagent comprising: an aqueous phase, a base, a group VIII metal as hydrogenation catalyst, and hydrogen dissolved in the aqueous phase, at a concentration in equilibrium with a gas phase whereof the partial pressure in hydrogen is not less than 50 kPa, advantageously ranging between 50 kPa and 2.10 7 Pa. The invention is applicable to organic synthesis.

19 Claims, No Drawings

SELECTIVE HYDRODEHALOGENATION METHOD

This application is an application under 35 U.S.C. Section 371 of International Application Number PCT/FR99/03031 filed on Dec. 07, 1999.

A subject matter of the present invention is the hydrogenolysis of heavy halogen carried by a carbon itself carrying at least one fluorine atom.

A more particular subject matter of the present invention is a process for producing compounds carrying a fluoro atom and a hydrogen atom on a carbon of $sp^3$ hybridization, said carbon itself carrying an electron-withdrawing functional group. The present invention relates more particularly to a liquid-phase process.

Fluorinated derivatives of aliphatic nature, that is to say fluorinated derivatives in which the fluorine is carried, at least in part, by an $sp^3$ carbon, are generally obtained by an exchange of fluorine with another halogen atom. This exchange is generally carried out by using hydrofluoric acid or else salts of hydrofluoric acid.

However, one of the problems encountered is that it is often difficult to carry out the exchange between the fluorine and a halogen with a higher atomic number when the halogen to be exchanged is carried by a carbon itself carrying a hydrogen atom.

This is why it is rather difficult to obtain compounds where an aliphatic compound carries both a hydrogen and at least one fluorine. One of the routes provided consists in dehydrohalogenating (that is to say, in removing a molecule of hydrohalic acid to give an ethylenic compound and then hydrogenating this ethylenic compound). This route is not possible for all compounds as a hydrogen is necessarily essential in the β position to achieve the removal of the hydrogen and the halogen which it is desired to remove.

Provision has been made, in patent GB 1 364 495, to synthesize certain monohydrogenated perfluorinated compounds (Rf-H) from the corresponding iodide (Rf-I) but this use of an iodinated derivative is very expensive and the pressure conditions disclosed in this document are very severe for kinetics which do not appear to be very high.

European patent application EP 0 726 244 discloses the reduction of a very specific cyclopropanic acid structure which, however, does not carry an electron-withdrawing group in in addition to a chlorine and a fluorine (although the acid functional group is certainly an electron-withdrawing group, it is not, however, connected directly to the carbon carrying the fluorine and the halogen).

Gas-route processes have also been provided (in particular EP 0 657 413 A) but, in addition to the disadvantages related to the gas route, it appears difficult to obtain a high selectivity at the same time as a high degree of conversion.

This is why one of the aims of the present invention is to provide a liquid-phase process which makes possible the replacement of a heavy halogen by a hydrogen, this replacement being carried out while a fluorine atom is carried by the same carbon as that which carries the halogen to be replaced by a hydrogen.

Another aim of the present invention is to provide a process of the preceding type which is selective with respect to fluorine.

Another aim of the present invention is to provide a process of the preceding type which is capable of giving good results with a compound which does not exhibit hydrogen β to the halogen to be made to leave.

Another aim of the present invention is to provide a process of the preceding type which is selective with respect to fluorine without requiring the use of iodide.

These aims, and others which will become apparent subsequently, are achieved by means of a selective hydrodehalogenation process (that is to say, the operation which consists in removing the halogen from a molecule by treating the latter by means of hydrogen to give, on the one hand, hydrohalic acid and, on the other hand, the starting molecule modified by the replacement of a halogen by a hydrogen) which comprises a stage in which a substrate exhibiting a carbon atom of $sp^3$ hybridization carrying:

at least one electron-withdrawing group (EWG) (that is to say, a group with a positive Hammett constant $\sigma_p$ or $\sigma_i$), at least one fluorine atom, and at least one halogen atom heavier than fluorine;

is brought into contact with a reactant comprising:

an aqueous phase, a base, a metal belonging [lacuna] Group VIII and to the fourth or to the sixth period of the Periodic Table as hydrogenation catalyst, and hydrogen dissolved in the aqueous phase, at a concentration in equilibrium with a gas phase, the hydrogen partial pressure of which is at least equal to 50 kPa, advantageously between 50 kPa and $2 \times 10^7$ Pa.

Of course, the aqueous phase is a liquid phase.

The present invention is targeted more particularly at the case where said atom of $sp^3$ hybridization carries two fluorine atoms.

The preferred electron-withdrawing functional groups are, on the one hand, optionally substituted aryls and, on the other hand, those for which the Hammett constant $\sigma_p$ is at least equal to 0.1 and it is also preferable for the inductive component of $\sigma_p$, $\sigma_i$ to be at least equal to 0.1, advantageously to 0.2, preferably to 0.3 (for example, cf. March, "Advanced Organic Chemistry", 3rd edition, John Wiley and Son, pages 242 to 250 and in particular Tables 4 and 5).

When there is only a single electron-withdrawing group (or functional group) and a single fluorine, it is desirable for one, preferably both, conditions below to be met:

either the electron-withdrawing group exhibits a $\sigma_i$ of greater than or equal to 0.15, advantageously at least equal to 2, preferably to 3;

or the halogen which has to be displaced is in the allylic position of a π bond (double, triple or aromatic bond, including carbonyl and nitrile bonds), it being possible for the π bond to belong to the electron-withdrawing group.

Mention may be made, among the electron-withdrawing groups (EWG), of:

substituted chalcogen atoms, aryl groups, groups exhibiting, as atom carrying the bond connecting it to the remainder of the molecule, a carbon atom connected to at least two fluorine atoms, chalcogens with an atomic number at least equal to that of perfluorinated sulfur (for example $SF_5$);

carboxylic, sulfonic and sulfinic functional groups, that is to say functional groups which derive from carboxylic, sulfonic and sulfinic acids [these functional groups can be the acid functional group proper (in the acid form or advantageously in the salified form) but also amides, imides and esters].

Generally, the process proceeds particularly well when the electron-withdrawing group (EWG) corresponds to a salified acid functional group.

In other words, the electron-withdrawing group (EWG) is then chosen from negatively charged groups.

Preference is given, among the metals from Group VIII, to those of the fourth period, in particular nickel and cobalt, and more particularly nickel. In the present application, reference is made to the Periodic Table of the Elements published in the supplement to the Bulletin de la Societe chimique de France in January 1966).

This is because the metals from the platinum group exhibit a relatively mediocre selectivity with respect to the fluorine to be removed. However, the platinum period is preferable to that of palladium.

The forms which are the most readily used in the process are the solid catalyst forms and more particularly, for nickel and cobalt, the "Raney" forms.

The preferred catalysts are catalysts based on Raney nickel, that is to say the catalysts for which the main active element, preferably the only active element, is Raney nickel.

The substrates generally do not exhibit more than 50 carbon atoms and even do not exhibit more than 25. However, it should be emphasized that the process does not exhibit the same limitations as the gas-phase routes and thus that the molecular mass does not have a critical nature.

To obtain a good yield and a good selectivity, it is highly desirable to carry out the reaction while maintaining the pH at a value sufficient to ionize the possible acid functional group and, more generally, at least equal to 4, advantageously to 7, preferably to 10.

The amount of base to be introduced into the reaction medium is at least equal to the amount necessary for the neutralization of the hydrohalic acid given off during the selective hydrodehalogenation and, if appropriate, the amount of base necessary for the neutralization of the acid functional groups of the substrate, when the latter exhibits such functional groups. It is rare for the amount of base to exceed three times and even twice the amount necessary for the neutralization of the hydrohalic acid given off and for the neutralization of the acid functional groups of the substrate.

Generally, the halogen heavier than fluorine is chlorine. In fact, chlorine is the preferred halogen not from a technical viewpoint but from an economic viewpoint. The choice of chlorine renders the selectivity of the hydrodehalogenation more difficult with respect to the fluorine. The present invention is of little advantage in the cases where the halogen is iodine; this is because the selectivity between fluorine and iodine is such that the effect of the present process is less marked than in the case of bromine and a fortiori of chlorine.

The hydrodehalogenation reaction is advantageously carried out at a temperature of between ambient temperature (approximately 20° C.) and approximately 150° C. In the present description, the term "approximately" is employed to emphasize the fact that the values which follow it correspond to values which have been mathematically rounded off and in particular that, when the figure or figures the furthest to the right of a number are zeros, these zeros are positional zeros and not significant figures, unless, of course, it is otherwise specified. In general, it is preferable to carry out the hydrodehalogenation at a temperature of between 30° C. and 100° C. (two significant figures).

The bases do not need to be completely soluble in the reaction medium. It is sufficient for them to be slightly soluble and for them to maintain the pH at the desired values.

Mention may in particular be made of oxides and basic salts of alkali metals or of alkaline earth metals, and the corresponding hydroxides.

Organic bases can also be used, either alone or to facilitate the transfer of the $OH^-/H^+$ ions. Mention may be made, among the latter, of ammonium hydroxides or primary, secondary or tertiary amines. Use may also be made of other phase transfer agents, in particular "cryptants", such as crown ethers.

When organic bases are used to facilitate the action of a base of low solubility (in particular an inorganic base), they can be used at a level of approximately 0.1 times the amount of substrate expressed in moles (or more generally in equivalent). In the case of the joint use of an inorganic base and of an amine, it is pointless for the amount of amine to be greater than 0.4 times the amount of substrate expressed in equivalent. The preferred amines are those which cannot be easily alkylated and in particular tertiary amines.

It may be advantageous to provide a third solvent to help the substrate to be at least partially soluble in the aqueous phase.

It is preferable to choose, as third solvent, one of the solvents which are miscible, partially or preferably in any proportion, with Water but is less polar than the latter.

It is preferable for these solvents not to be capable of being hydrogenated under the reaction conditions. This restriction can result in the exclusion in particular of ketones and nitriles or in the choice of mild conditions.

Consequently, among the solvents which may be envisaged, mention should be made of ethers, alcohols and their mixtures.

More generally, it is desirable for the constituents of the reaction mixture and in particular the substrate not to comprise a functional group capable of being hydrogenated under the reaction conditions.

The substrates correspond in general to the following general formula:

$$EWG-CFX-Y$$

where X represents a halogen of a higher rank than that of fluorine (that is to say, essentially chlorine and bromine, preferably chlorine);

where Y represents a hydrogen (but this is not the preferred value), a halogen atom (advantageously a fluorine), an advantageously electron-withdrawing carbonaceous radical or even an electron-withdrawing group (as defined in the present description and in particular below);

where EWG represents an electron-withdrawing group, the possible functional groups of which are inert under the reaction conditions.

The total carbon number of the substrate advantageously being within the closed range 1 to 15, preferably 2 to 10 (apart from the carbonaceous part of the amide, imide or ester functional groups, when the substrates are acids in one of the above forms).

Y is advantageously:

fluorine if it is desired to obtain a monofluorinated methyl ($-CH_2F$), Y can have the same values as X with the same subpreferences a residue of formula (II) $R-(C\Xi_2)_p-$ where the $\Xi$ groups, which are alike or different, represent a fluorine or a perfluorinated radical of formula $C_nF_{2n+1}$ with n an integer at most equal to 8, advantageously to 5;

where p represents an integer at most equal to 2;

where R is a hydrogen atom, a fluorine atom or a hydrocarbonaceous radical, advantageously an alkyl or aryl radical.

It is desirable for EWG to be chosen from:

aryls in which the nucleus is advantageously depleted in electron (homocycle carrying an electron-withdrawing functional group or 6-membered heterocycle);

acid functional groups (that is to say, carrying acidic hydrogen, advantageously for which the pKa is at most equal to 7, preferably to 4); it is advisable to choose the acid functional groups from those in which the proton is carried by a metalloid, advantageously by a chalcogen atom, preferably by an oxygen atom;

an alkyloxyl radical; in this case, EWG advantageously corresponds to the formula
—O—$(CH_{2-m}\Xi_m)_p$—R (cf. below).

It is thus advantageous for EWG to correspond to the formula (III) —Z—H or —Z$^-$, in which Z represents a bivalent radical advantageously chosen from —C(O)—O—; —S(O)—O—; —S(O)$_2$—O$^-$.

Mention may more particularly be made, among the preferred substrates, of carboxylic acids mono- or bifluorinated on a carbon atom carrying the carboxylic functional group and, in particular, those in which the a carbon is both chlorinated and fluorinated.

Mention may also be made of aralkyls in which the carbon in the benzyl position is fluorinated and chlorinated.

Finally, mention may be made, as substrates exhibiting a specific nature and a particular advantage, of ethers, at least one of the carbons of which which carry the ether functional group is both chlorinated and fluorinated, in which EWG corresponds to the formula:

—O—$(CH_{2-m}\Xi_m)_p$—R where the groups, which are alike or different, represent a fluorine or a perfluorinated radical of formula $C_nF_{2n+1}$ with n an integer at most equal to 8, advantageously to 5;

where p represents an integer at most equal to 2;

where the m values, which are alike or different, represent zero or an integer at most equal to 2;

where R is a hydrogen atom, a fluorine atom or a hydrocarbonaceous radical of at most 10 carbon atoms, advantageously an alkyl or aryl radical.

The values of m, of X and, when p is equal to 1, of R are advantageously chosen so that the link carrying the oxygen exhibits at least one hydrogen atom and one fluorine atom; this can be advantageous in particular during the synthesis of anesthetic ethers, such as desflurane.

The process is particularly advantageous for substrates not exhibiting hydrogen β to the halogen to be hydrodehalogenated (see the presentation of the problem in the introductive part).

The substrate can, but this is only rarely of advantage, comprise several sites of EWG-CFX-type, in which case the various X groups will be simultaneously replaced by hydrogen.

The process has proved to be particularly advantageous for fluorinated carboxylic acids in which the α carbon is chlorinated, in particular chloro-difluoroacetic acid, which makes it possible to obtain difluoroacetic acid.

These carboxylic functional groups which have been spoken of previously are advantageously used in the form of salts, generally alkaline salts, of acid.

However, they can be used in other forms, in particular the functional groups derived from the acids which were mentioned above (for example, ester, imide or amide).

The stoichiometry of the reaction is:

EWG-CFX-Y+H$_2$→HX+EWG-CFH-Y and, when Y is chosen from the values of X:

EWG-CFX-Y+2H$_2$→HX+HY+EWG-CFH$_2$

The following nonlimiting examples illustrate the invention:

EXAMPLE 1

57 g of water are introduced into a 300 ml Sotelem reactor made of Hastelloy HB2, stirring is begun and 57 g of chlorodifluoroacetic acid (0.44 mol) are added while cooling. 137 g of a 10N aqueous sodium hydroxide solution (approximately 1.2 mol) are introduced, still while cooling. 1 g of Raney nickel is subsequently added. The reactor is closed and purging is carried out with nitrogen, with 2 times 10 bar, and with hydrogen, with 2 times 10 bar.

The reactor is placed under a pressure of 20 bar and heating is carried out at 70° C. while stirring. The reactor is kept under constant pressure of 20 bar. When hydrogen consumption ceases, these conditions are maintained for a further 15 min and then the reactor is cooled to 20° C.; the hydrogen consumption is then substantially equal to the stoichiometric amount. Purging is carried out with nitrogen, with 2 times 10 bar.

The catalyst is filtered off. By analysis of the reaction medium by ion-exchange chromatography, a DC of 99.8% is obtained with a sodium difluoroacetate RY of 98.7%.

COMPARATIVE EXAMPLE 2

The reaction is carried out as in Example 1 but using, as catalyst, 0.50 g of Pd/C comprising 5% of palladium. The results are as follows: Hydrogen consumption= approximately 50% of the SA (that is to say, Stoichiometric Amount):

DC=25%

RY$_{sodium\ difluoroacetate}$=12%

CY=50%

RY$_{sodium\ acetate}$=10%

COMPARTIVE EXAMPLE 3

The reaction is carried out as in Example 1 but dispensing with the sodium hydroxide. The results are as follows:

Hydrogen consumption=approximately 10% of the SA (that is to say, Stoichiometric Amount):

DC<10%

Presence of a significant amount of fluorine ion

Presence of acetic acid

Presence of nickel fluoride

Presence of a very small amount of DFA (difluoro-acetate difluoroacetic).

What is claimed is:

1. A selective hydrodehalogenation process, comprising the step of contacting a substrate of the formula;

of the formula:

EWG-CF$_2$H wherein X represents a halogen atom heavier than fluorine and EWG represents an electron-withdrawing group inert under the reaction conditions, with a reactant comprising an aqueous phase, a base, a metal from Group VIII and from of the fourth or the sixth period of the Periodic Table, and hydrogen dissolved in the aqueous phase, at a concentration in equilibrium with a gas phase, at a hydrogen partial pressure at least equal to 50 kPa to produce a product of the formula:

EWG-CF2H wherein EWG is defined above.

2. A process according to claim 1, wherein the hydrogen partial pressure is between 50 kPa and $2 \times 10^7$ Pa.

3. A process according to claim 1, wherein the electron-withdrawing group is an aryl, a carboxylic group, a sulfonic group, a sulfinic groups, or an atom carrying at least two fluorine atoms.

4. A process according to claim wherein 1, the electron-withdrawing group is a negatively charged group.

5. A process according to claim 1, wherein the metal from Group VIII and from of the fourth or the sixth period of the Periodic Table, is Nickel or Cobalt.

6. A process according to claim 5, wherein the metal from Group VIII and from of the fourth or the sixth period of the Periodic Table, is in the "Raney" form.

7. A process according to claim 1, wherein the metal from Group VIII and from of the fourth or the sixth period of the Periodic Table, is Raney nickel.

8. A process according to claim 1, wherein the aqueous phase is maintained at a pH value at least equal to 4.

9. A process according to claim 1, wherein the aqueous phase is maintained at a pH value at least equal to 7.

10. A process according to claim 1, wherein the aqueous phase is maintained at a pH value at least equal to 10.

11. A process according to claim 1, wherein the substrate is an acid, the amount of base being at least equal to the amount necessary for the neutralization of said acid, and at least equal to the amount of a hydrohalic acid given off by the selective hydrodehalogenation.

12. A process according to claim 1, wherein the halogen heavier than fluorine is chlorine.

13. A process according to claim 1, wherein contacting is carried out at a temperature between ambient temperature and 150° C.

14. A process according to claim 13, wherein the temperature is between 30° C. and 100° C.

15. A process according to claim 1, wherein the base is an alkali metal ammonium hydroxide, an alkaline earth metal ammonium hydroxide, an alkali metal carbonate, an alkaline earth metal carbonate, a basic salt of an alkali metal, a basic salt of an alkali metal, an ammonium or a mixture thereof.

16. A process according to claim 1, wherein the aqueous phase comprises a solvent to help in dissolving the substrate, said solvent being miscible in any proportion with water and less polar than water.

17. A process according to claim 1, wherein the solvent is an ether, an alcohol, or a mixture thereof.

18. A process according to claim 1, wherein the substrate is a fluorinated carboxylic acid comprising a chlorinated α carbon, an aralkyl comprising a fluorinated and chlorinated carbon in a benzyl position, or an ether comprising at least one chlorinated and fluorinated carbon carrying an ether functional group.

19. A process according claim 1, wherein the substrate is chlorodifluoroacetic acid.

\* \* \* \* \*